(12) United States Patent
Khan

(10) Patent No.: US 10,327,480 B2
(45) Date of Patent: Jun. 25, 2019

(54) DISPOSABLE LINERS FOR BODY AREAS

(71) Applicant: Misbah Khan, New York, NY (US)

(72) Inventor: Misbah Khan, New York, NY (US)

(*) Notice: Subject to any disclaimer, the term of this patent is extended or adjusted under 35 U.S.C. 154(b) by 671 days.

(21) Appl. No.: 14/977,064

(22) Filed: Dec. 21, 2015

(65) Prior Publication Data

US 2017/0172218 A1 Jun. 22, 2017

(51) Int. Cl.
| | | |
|---|---|---|
| *A41B 9/12* | (2006.01) | |
| *A61L 15/40* | (2006.01) | |
| *A61L 15/46* | (2006.01) | |
| *A61F 13/14* | (2006.01) | |
| *A61F 13/15* | (2006.01) | |
| *A61F 13/47* | (2006.01) | |
| *A61F 13/84* | (2006.01) | |
| *A61F 13/00* | (2006.01) | |

(52) U.S. Cl.
CPC .......... *A41B 9/12* (2013.01); *A61F 13/00* (2013.01); *A61F 13/14* (2013.01); *A61F 13/15* (2013.01); *A61F 13/47* (2013.01); *A61F 13/8405* (2013.01); *A61L 15/40* (2013.01); *A61L 15/46* (2013.01); *A41B 2400/36* (2013.01); *A41B 2400/60* (2013.01); *A61L 2300/30* (2013.01); *A61L 2300/404* (2013.01); *A61L 2300/624* (2013.01); *A61L 2400/12* (2013.01)

(58) Field of Classification Search
CPC ... A41B 2400/36; A41B 2400/60; A41B 9/12; A61F 13/00; A61F 13/14; A61F 13/15; A61F 13/8405; A61L 26/0004; A61L 26/0066

See application file for complete search history.

(56) References Cited

U.S. PATENT DOCUMENTS

| | | | | |
|---|---|---|---|---|
| 4,393,521 A * | 7/1983 | Jones | .............. | A41D 27/13 2/56 |
| 5,042,088 A * | 8/1991 | Sherrod | .............. | A41D 27/13 2/53 |
| 5,603,653 A * | 2/1997 | Hartman | .............. | A41B 9/12 2/267 |
| 5,858,014 A * | 1/1999 | Kepes | .............. | A61F 13/141 604/385.07 |
| 6,203,810 B1 * | 3/2001 | Alemany | .............. | A41D 27/13 424/400 |
| 6,653,524 B2 * | 11/2003 | DeLucia | .............. | A61F 13/8405 604/364 |
| 2002/0026165 A1 * | 2/2002 | Elder | .............. | A61F 13/51305 604/364 |
| 2003/0083632 A1 * | 5/2003 | Rubio | .............. | A61F 13/47236 604/385.01 |
| 2005/0115462 A1 * | 6/2005 | Disalvo | .............. | A61F 13/8405 106/403 |
| 2005/0136773 A1 * | 6/2005 | Yahiaoui | .............. | A61F 13/537 422/394 |

(Continued)

*Primary Examiner* — Peter S Vasat
(74) *Attorney, Agent, or Firm* — Wiggin and Dana LLP; Gregory S. Rosenblatt

(57) ABSTRACT

Body liners for absorbing sweat and masking or adsorbing odors occurring in breast, panty, and underarm areas are sized according to area and have mesh top surface, cotton central layer and bottom surface. The mesh top surface is coated for silkiness, the central layer impregnated with plant extracts for anti-inflammatory properties, fragrance, and odor masking. Liners may line garments, or have adhesive for adhering to skin.

17 Claims, 7 Drawing Sheets

(56) References Cited

U.S. PATENT DOCUMENTS

| | | | | |
|---|---|---|---|---|
| 2010/0152687 A1* | 6/2010 | Carlozzi | ................ | A41B 9/04 |
| | | | | 604/359 |
| 2011/0105623 A1* | 5/2011 | Benjamin | .............. | A61K 31/10 |
| | | | | 514/711 |
| 2013/0236523 A1* | 9/2013 | Webster | ................ | A01N 59/02 |
| | | | | 424/409 |

* cited by examiner

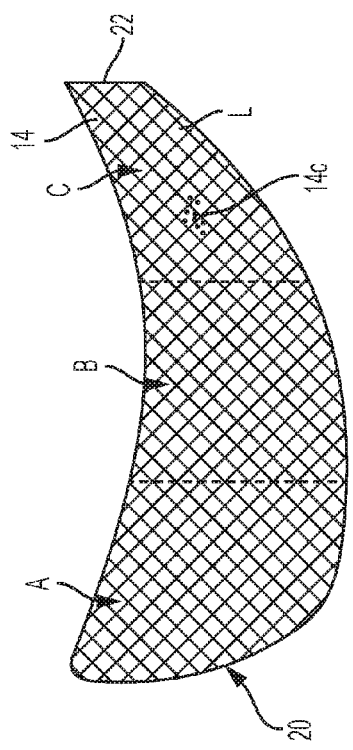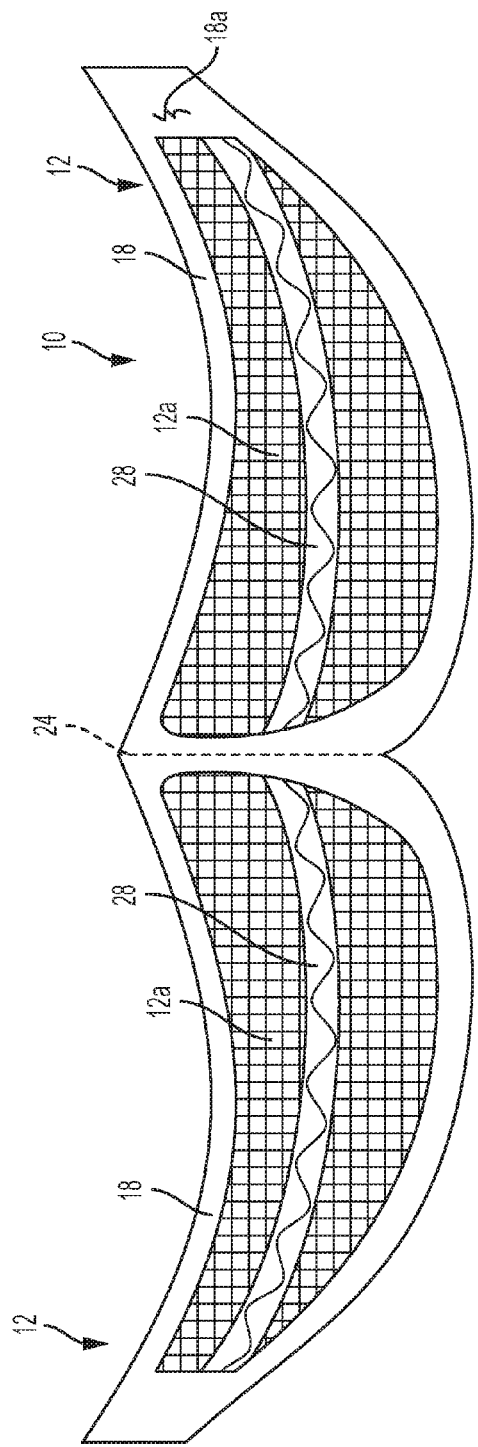

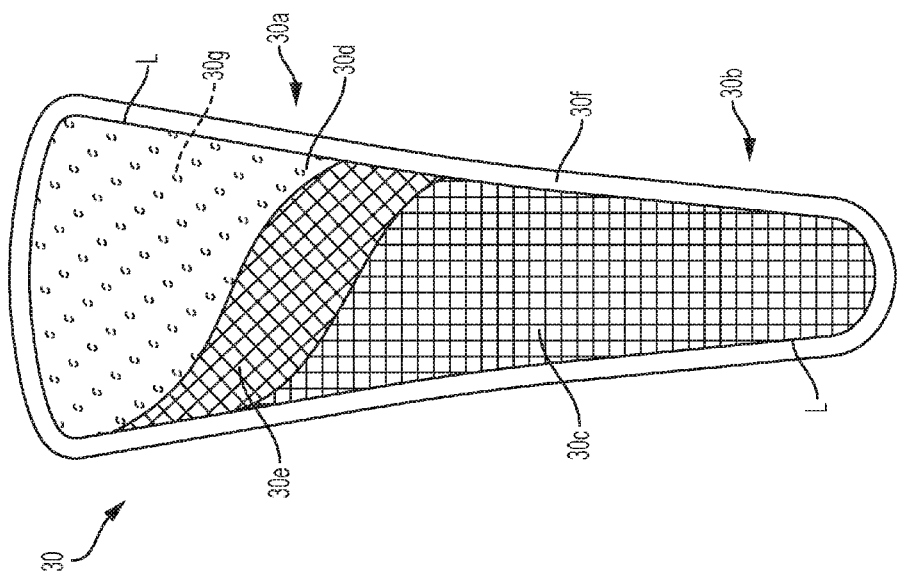
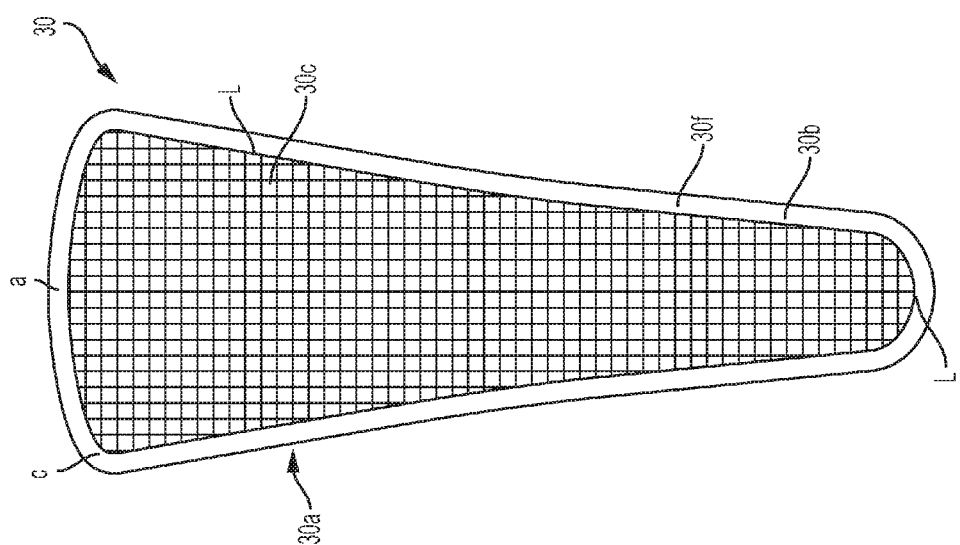

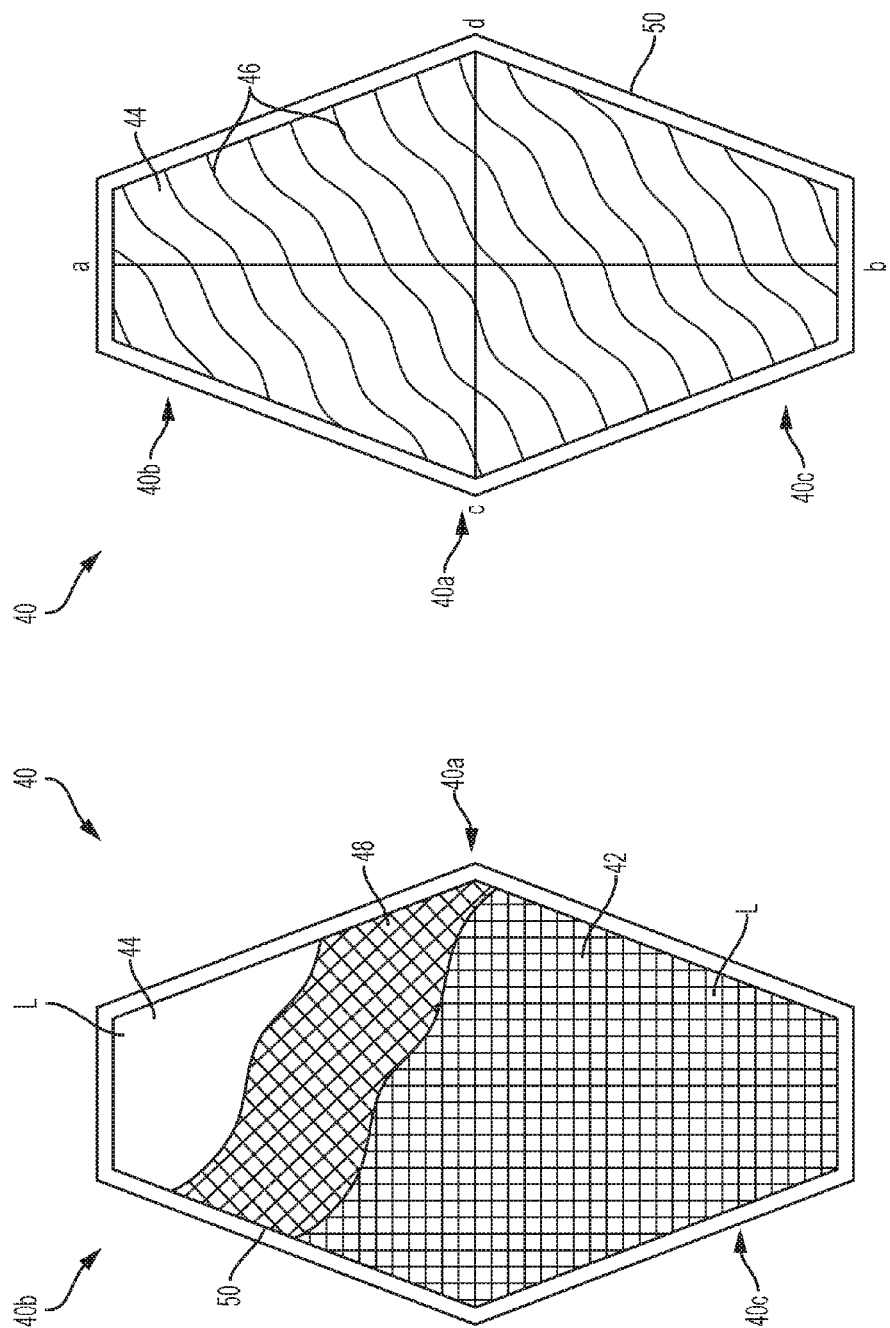

DISPOSABLE LINERS FOR BODY AREAS

FIELD OF THE INVENTION

This invention relates to disposable liners for body areas so as to solve the problems of sweat, body odor, and moisture in private parts of the body and their socially embarrassing and skin disorder consequences.

BACKGROUND OF THE INVENTION

Sweat, body odor, and moisture in private parts of the body are not only socially embarrassing but can also be a cause of skin disorders such as infections, itchy rashes, chaffing, and maceration. Daily showers along with use of astringents and undergarments provide a reasonable amount of hygiene, however, these measures do not last long enough and moisture continues to build throughout the day especially on hot humid days.

Sweat is produced from special glands in the skin called eccrine glans (sweat glands). These glands cover most parts of the body. Sweat mostly consists of minerals, urea and lactate, and is produced mostly in response to temperature regulation and under emotional circumstances, and has a pH of 4.0-7.0 (acidic to neutral). Sweat can start as hyperosmolar (higher salt concentration) and can become hypoosmolar (low salt concentration) depending upon the amount of sweat produced. On average, humans produce anywhere from 2-10 liters of sweat per day (depending upon lifestyle, temperature changes, diet and genetics).

The most common skin diseases in private parts due to retention of sweat and moisture are:
  (i) Fungal infections: yeast; seborrheic dermatitis;
  (ii) Bacterial infections: erythrasma (*corynebacterium minutissimum*); trichomycosis (*corynebacterium tenius*);
  (iii) Inflammatory conditions: acne; cysts; hidradenitis suppurativa, and
  (iv) Contact dermatitis: intertrigo; chromhydrosis; bromhydrosis (yellow/orange stains).

Currently available treatment options for skin rashes due to moisture trapping include prescription medications for at least 2-4 weeks; over the counter deodorants, astringents, corn starch powder, sprays, foams, soaps enriched with liquorice, chlorophyllin, and ribwort. Also available are re-usable/washable bar liners made of cotton, as well as disposable panty liners & underarm liners made of a thin absorbing material with or without fragrance.

Odor comes from apocrine glands that are mostly present in axillary, pubic, mammary/areolar areas, and the naval. The composition of odor is determined genetically (major histocompatibility molecules aka, MHC-molecules). Odor is secreted by apocrine glands along with eccrine/sweat glands and consists of unsaturated fatty acids, odiferous steroids and is carried to the surface by odor-binding proteins. Skin flora (bacteria that normally live on us) produce enzymes that convert the fatty acids into chemicals that produce odor with the help of lipases (enzymes that breakdown fats).

Types of Odor are:
  (i) *Corynebacterium* (lives on heavy sweat areas): produces lipases that breakdown the fatty acids into butyric acid (typical odor smell);
  (ii) Propionibacteria (lives in acne prone areas): breaks down amino acids into propionic acid (vinegar like smell) and;
  (iii) *Staphylococcus epidermidis* (particularly groin areas): produces isovaleric acid which gives a rather cheesy odor.

Currently available measures to prevent and counteract odor such as deodorants, talcum powder, perfumes in addition to daily showers provide temporary relief lasting a few hours against the unpleasant body odor but fail to provide any long-term benefits especially in sensitive areas such as under the breasts and pubic/genital areas.

Astringents, deodorants, and perfumes cannot be repeatedly applied throughout the day on sensitive areas without running into the risks of skin dryness, itching, flaking and rashes due to irritant contact dermatitis (a type of a skin rash which is a reaction to higher concentration of a certain irritant), which can be quite uncomfortable. Constant skin itching can lead to breakdown of the skin barrier, which further opens doors to various skin infections (bacterial, fungal, etc.)

One of the currently available measures to help control moisture and odor in pubic/genital areas consists of a liner with an adhesive surface on the back and a thin mesh on the top which can be adhered to the inside of a panty. This type of a liner so-called "panty-liner" provides an extremely thin layer of a mesh for the moisture collection. There is no active ingredient in the liner itself that will prevent skin inflammation, neutralize odor, and adsorb moisture thereby preventing repeat skin infections while providing the appropriate hygiene that will last all day long. Additionally, there is no hygiene liner for people who do not wear undergarments as all currently available panty-liners can only be worn in conjunction with an undergarment.

A currently available bra-liner comes as a wide cotton belt, is tucked under the bra for the intended use, and is visible from the outside. The bra-liner is washable, non-disposable, of questionable hygiene, and being visible lacks privacy. The bra-liner is non-adhesive, has no active ingredient, and no medical benefit.

A currently available underarm-liner consists of a top mesh, a thin layer of pressed cotton, and a back with an adhesive for sticking onto the shirtsleeve. The liner is designed to be smaller in the center (site of maximum sweat production) and much wider at the edges (site of least sweat production). The central layer of cotton is devoid of any active ingredients. None of the currently available liners has a thickness gradient and their thickness is uniform throughout the length of the liner. The pattern and design of the top surface depends on the brand. The liners are not self-adhesive and need to be pasted onto the shirtsleeve or secured by a harness to the skin surface. The liners are disposable and have no medical and no preventative benefits.

There is a need for hygiene products that provide moisture and odor control in private parts of the body (pubic/genital areas, under the breasts, and underarms) throughout the day without the adverse effects of skin irritation; and that prevent skin rashes commonly seen in moisture-rich areas of the body.

There is a need for a specific kind of a liner that can provide the desired amount of hygiene for at least 24 hours, is easy to use, will provide preventative medical benefits in addition to alleviating moisture, odor, and stains; and is affordable.

Specifically, there is need for a series of liners that can be used on the undersurface of shirts, brassieres, and panties ranging in sizes and applicability based on the customer's needs such as, mild to moderate sweaters, heavy sweaters, customers with frequent yeast infections, with odor problems, or with itchy rashes. The liners with an adhesive surface to adhere to the inside of the undergarments such as brassieres, panties and shirts as well as a self-adhering surface that will adhere to the skin itself thereby eliminating the need for an undergarment for its proper use.

SUMMARY OF THE INVENTION

The present invention provides designs for a series of undergarment liners and spray-on elixir that specifically improve hygiene in men and women; to prevent frequent infections from certain bacteria and fungi that grow rapidly in sweat and moisture; to prevent itchy rashes due to irritation from skin maceration; and to prevent stains on garments and undergarments.

The invention also provides a design for sanitary pad that can be used by women during menstrual cycle which will not only provide a highly absorbent surface but will also be hygienic and prevent bacterial overgrowth. Other variations of invention can be provided as specific embodiments adopted for specific body areas, and can be designated as specific product lines with variations of active ingredients.

One product line comprises of a set of thin liners with an adhesive back, each specifically designed to fit on the underside of a shirtsleeve, brassiere and panties, with an easy to use peel and stick method.

A second line comprises of a set of liners each specifically designed to fit a body area and having an adhesive surface that can stick directly to the surface of the skin thereby eliminating the need for a garment or an undergarment using the same easy to peel and stick method.

The liners have a water-repellant surface (non-permeable) on the back and have a water-absorbing (permeable) surface on the top, the side that is in contact with the skin surface.

In one embodiment of the invention the liner central layer includes a thin layer of cotton impregnated with one or more active ingredients 14c. The active ingredients can serve as a fragrance, natural anti-inflammatory extracts, medicinal and other therapeutic purpose extracts, encapsulated into selenium nanoparticles, an anti-fungal agent including Miconazole 2% which is an FDA-approved over the counter (OTC) powder/lotion/spray product.

The central layer may be impregnated with aluminum and/or magnesium hydroxide stearate and corn starch and/or other non-active ingredients for better hygiene among other things.

Encapsulated droplets activate upon peeling away a protective sticker, and by contact with moisture.

For the product line with the adhesive on the back (i.e., garment side), the entire back surface has a thin layer of adhesive.

For the product line with self-adhesive surface, the top surface has adhesive stripes on the top surface of the water permeable mesh and at the edges to ensure a proper seal with the surface of the skin.

The invention further provides for the opportunity to include other active and non-active ingredients, including admixture of extracts of white grapes, mint, rosemary, hibiscus flower extract and cucumber in various combinations/concentrations which can be encapsulated in conjunction with selenium, i.e., microencapsulated extracts and fragrances. The microencapsulated extracts and fragrances will release upon contact with the surface of the skin and moisture on the surface of the skin. Other active ingredients can be included and/or added to the device of encapsulated extracts and fragrances, such as plants with anti-inflammatory and odor masking properties in conjunction with selenium nanoparticles that have antibiotic properties. Furthermore, other ingredients can include Miconazole 2% powder/lotion/spray which can be incorporated into the device for its anti-fungal properties.

The formulation of all aforementioned active ingredients in an aqueous base is intended to be disposed into an area of the liners and dispensed as an elixir for spray/direct application to the affected areas on the body.

Accordingly, the invention provides a liner for absorbing excessive moisture from sweat; adsorbing body odor; absorbing body fluids, including but not limited to, sweat, moisture and menstrual flow, among other things. In addition, the invention to provide a liner that prevents bacterial overgrowth; prevents fungal overgrowth; prevents skin chaffing in private parts; prevents skin maceration in private parts; prevents repeat skin infections in consumers who suffer from frequent rashes in private parts due bacterial and/or fungal overgrowth; prevents bacterial overgrowth in an environment/device enriched with body fluids such as moisture, sweat and menstrual flow providing multiple benefits.

Accordingly, an embodiment of a liner according to the invention includes a thin liner with an adhesive back, designed to fit on the underside of a shirtsleeve, brassiere and panties, easy to use peel and stick method. A further embodiment includes a liner with an adhesive surface that can stick directly to the surface of the skin thereby eliminating the need for a garment or an undergarment using the same easy to peel and stick method. In addition, the liners can have a water-repellant surface (non-permeable) on the back. The liners have a water-absorbing (permeable) surface on the top, i.e. the side that is in contact with the skin surface.

A central layer is also provided comprising of a thin layer of pressed cotton impregnated with active ingredients to serve as fragrance, natural anti-inflammatory extracts encapsulated into Selenium nanoparticles and an anti-fungal powder/lotion/spray consisting of Miconazole 2% which is an FDA-approved over the counter (OTC) product sold all over the world.

An embodiment of a liner according to the invention is not a substitute for prescription medications and preferably would not require a doctor's prescription for daily use.

Specific examples are included in the following description for purposes of clarity, but various details can be changed within the scope of the present invention.

OBJECTS OF THE INVENTION

An object of the invention is to provide a series of body area undergarment liners to improve hygiene in men and women; to prevent frequent infections from certain bacteria and fungi that grow rapidly in sweat and moisture; to prevent itchy rashes due to irritation from skin maceration; and to prevent stains on garments and undergarments.

An object of the invention is to provide a series of body area liners applied to the skin to improve hygiene in men and women; to prevent frequent infections from certain bacteria and fungi that grow rapidly in sweat and moisture; to prevent itchy rashes due to irritation from skin maceration; and to prevent stains on garments and undergarments.

Another object of the invention is to provide a liner that can deliver a combination of specifically chosen extracts of plants in various combinations/concentrations that are encapsulated extracts and fragrances and/or other specifically chosen active ingredients to release upon contact with the surface of the skin and moisture on the surface of the skin to address the exuded body fluids and associated bacteria that the active ingredients are intended to remedy.

Another object of the invention is to provide a liner having at least one added ingredient with anti-inflammatory and odor masking properties in conjunction with Selenium nanoparticles that have antibiotic properties, in addition to extracts and fragrances of plants.

Other and further objects of the invention will become apparent with an understanding of the following detailed description of the invention or upon employment of the invention in practice.

BRIEF DESCRIPTION OF THE DRAWINGS

Preferred embodiments of the invention have been chosen for detailed description to enable those having ordinary skill in the art to which the invention appertains to readily understand how to construct and use the invention and is shown in the accompanying drawing in which:

FIG. 3 is a plan view of the top surface of a component of the bra-liner of FIG. 1.

FIG. 4 is a plan view of the top surface of a preferred embodiment of bra-liner.

FIG. 6 is a plan view of top surface of panty-liner according to the invention.

FIG. 7 is a plan view of the panty-liner of FIG. 6 having a cut-away view showing top, central, and bottom layers FIG. 8 is a plan view of preferred embodiment of under-arm liner having a cut-away view showing its bottom surface.

FIG. 9 is a plan view of top surface of underarm liner of FIG. 8.

DETAILED DESCRIPTION OF PREFERRED EMBODIMENTS

Figure 1:
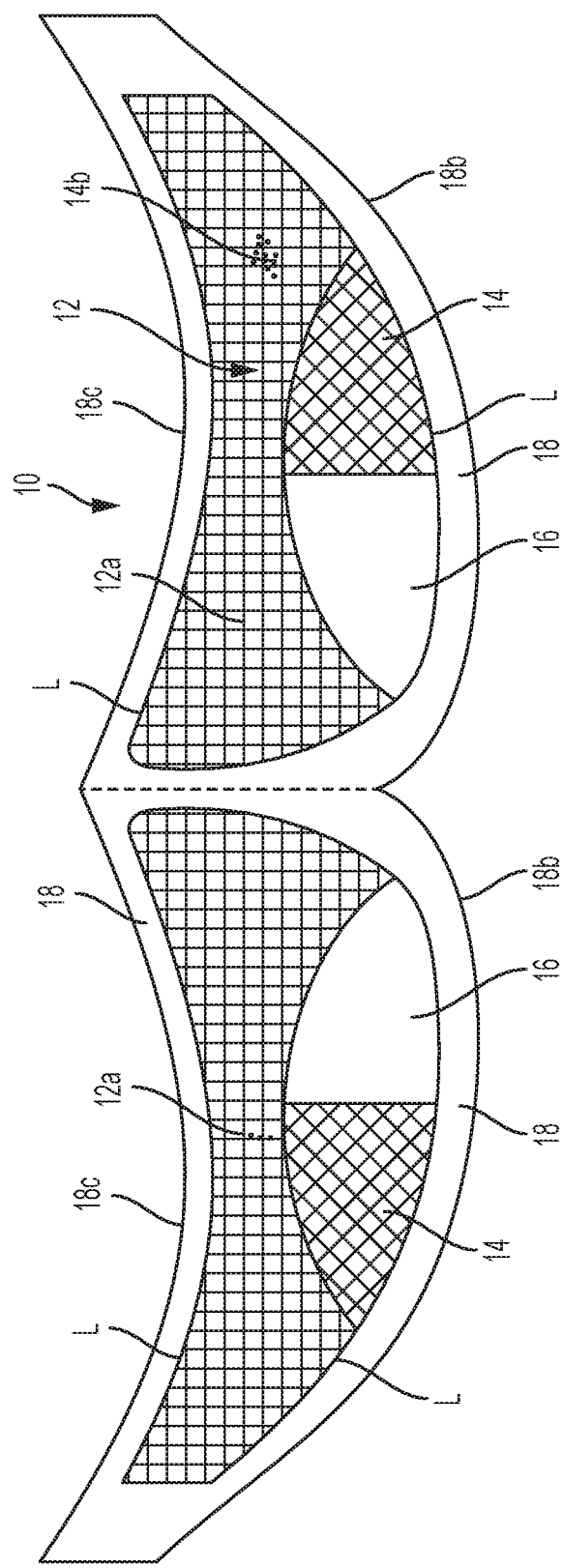
FIG. 1 is a plan view of the top surface of preferred embodiment of bra-liner according to the invention.
Figure 2:
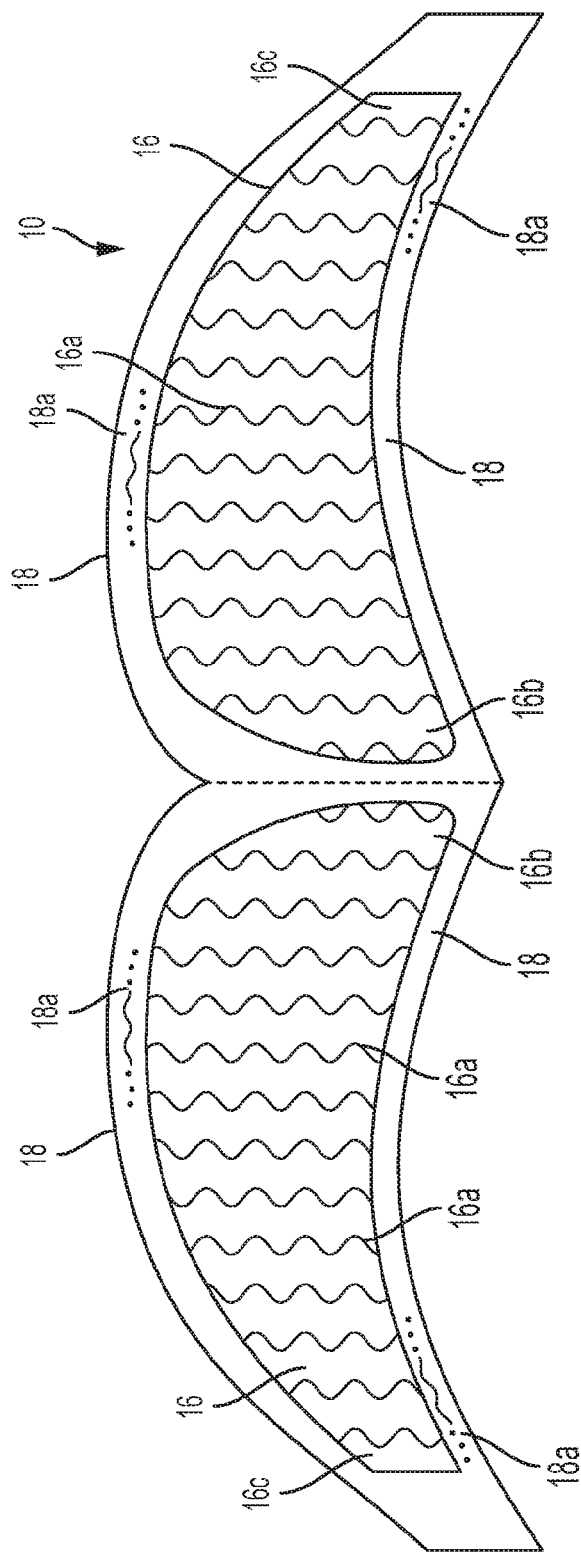
FIG. 2 is a plan view of bottom surface of bra-liner of FIG. 1.

Referring to FIGS. 1-3, bra-liners 10 have top 12 and bottom 16 surfaces comprising water-permeable top surface and water-impermeable bottom surface. Both surfaces are preferably made of transparent material. In this description the top surface of the liner when in use, is placed in contact with the skin.

The top surface 12 comprising of a thin mesh 12a filling the entire area within a perimeter line L. The mesh can be coated with an active ingredient such as dimethicone, silicone, selenium nanoparticles and/or talcum powder. The mesh allows the droplets of sweat and moisture to be diffused through it in order to be absorbed by a central liner layer 14 leaving the top surface completely dry. In addition, a top coating of dimethicone and/or talcum can be provided on the top surface 12 which allows for a rather silky smooth surface that will prevent chaffing, rubbing against the skin, irritation from the liner, and yet be hypoallergenic at the same time.

The bottom layer 16 comprises an extra-thin plastic/polyester layer that will provide the grounds for all the layers of the liner. In addition, the backside of the bottom layer can include an adhesive 16a on it.

A central liner 14 is tightly encased between the top 12 and bottom 16 layers.

Top and bottom layers taper at the edges in the form of a thin transparent edge 18 (preferably approx. 0.5 cm wide) which is consistent throughout the entire edge of the liner. The transparent edge may, or may not have the adhesive on its backside.

As shown in FIG. 1 the top surface, central layer and bottom surface each fill entire area of bra-liner within perimeter line L. In FIG. 1, top surface and central layer are broken away to show surfaces beneath.

The central layer (FIG. 3) is comprised of loosely packed cotton fibers instead of a pressed cotton sheet. The thickness of the central layer preferably varies anywhere from 1-mm to 10-mm. For a typical small-sized bra-liner for mild to moderate sweating the central layer will be 1-2 mm thick with a thickness gradient varying from being thicker towards the wider edge 20 (facing the center of the chest) to thinner at the narrower edges 22. In FIG. 3, a central layer thickness preferably varies from 2-3 mm in area A toward wider edge, 1-2 mm in center area B, and 1 mm at edge area C. The color of the central layer may be pure white, shades of white, shades of nude color or purely nude.

In one embodiment of the invention, the central layer 14 of loosely packed cotton fibers is impregnated with effective amounts of one or more active ingredients 14c. Active ingredients include including natural extracts of grape, cucumber, grape seed oil, hibiscus flower extract, rosemary, rosebud, menthol and/or mint encapsulated with selenium nanoparticles. The active ingredients 14c can be provided as an admixture of a proprietary blend of said ingredients in proportion to the expected ratio of aquaphilic and oleophilic counterparts expected to be provided in different specific embodiments to address varying circumstances, as well as hyper-osmolar or hypo-osmolar conditions, and/or bacterial products associated with a body area, such as butyric acid, propionic acids and/or isovaleric acids.

These plants/extracts are chosen based on their anti-inflammatory properties, their pleasant fragrances, and on their odor-masking properties, as more fully described below. The selenium nanoparticles are chosen based on its antibiotic properties especially against bacteria localized to the private parts of human body. These plants/extracts are impregnated onto the central layer cotton fibers in the form of selenium encapsulated micro-spheres/nanoparticles that activate upon peeling away a product protective sticker and upon contact with moisture. In another embodiment of the invention, an encapsulation device is provided to encapsulate an active ingredient. The encapsulation device can be disposed in or proximate to the center layer and includes at least one active ingredient such as dimethicone and talcum, fragrance, or odor eliminating ingredients. The encapsulation device is provided as a controlled or extended release of active ingredients and thus provides an improved solution to sweat, body odor and moisture.

The encapsulation device can be provided as a container, a strip, micro bead, nanoparticles, and/or a pellet, among other things. The container can be provided as a sphere or pill shape and formed from a dissolvable or otherwise degradable material containing the active ingredient, whereupon after a period of time upon exposure to air or breaking a seal of the container, can release all or a portion of the active ingredient. In addition, or in the alternative, the container can be a crushable material whereby upon crushing the active ingredient is released. Alternatively, the release of the chemical can be caused by the rupture of the microspheres/nanoparticles after contact with body moisture or mutual friction when the liner is in use.

In addition, or in the alternative, a strip impregnated with one or more active ingredients can be disposed in or proximate to the central layer 14. A protective sticker can be included on the liner prior to using the liner. Once the user peels away the protective sticker and the liner has contact with moisture the fragrance will release along with the dimethicone and talcum to provide the user protection.

The loosely packed cotton fibers of the central liner 14 slowly release fragrance upon rubbing/friction with the user's skin so that the liners maybe used for a long term yet temporary period. The scented ingredients are intended to release a pleasant smell. This process is also used to dissolve the dimethicone, talcum and deliver such ingredients to the user to resolve the issue of sweat, body order, and irritation to the skin.

Additionally, each active ingredient (the dimethicone, talcum, fragrance and odor eliminating ingredients) can be combined as an admixture. The ingredients do not chemically react with each other. Each ingredient responds to the body's release of either moisture, oil, or odor, but not necessary all at once. For example, the dimethicone and talcum react to the moisture and oil the body produces. These active ingredients combat the chaffing and rubbing of the undergarments on the body. The fragrance or odor eliminating ingredients release to reduce the foul odor produced by the users sweat, moisture and/or oils from the body. Each active ingredient does not depend on the other active ingredients to continue to deliver the active ingredients to the user. Accordingly, the liner can be effective under varying circumstances.

In one embodiment for bra liners, the composition of active ingredients which can be provided in an aqueous solution (for anti-inflammatory properties) is preferably:

1. Grape seed oil 10%-20%
2. Rosemary 10%-20%
3. Mint 5%-10%
4. Cucumber 10%-20%
5. Menthol 20%-30%

The formulation of all aforementioned active ingredients in an aqueous base is intended to be disposed into an area of the liners and/or dispensed as an elixir for spray/direct application to the affected areas on the body.

The bra liner can be enriched with any or all of the components of the active ingredients and enhanced with artificial fragrances.

The composition of an elixir for general application is preferably:

1. Grape seed oil 1%-50%
2. Rosemary 10%-50%
3. Mint 10%-50%
4. Cucumber 10%-20%
5. Menthol 5%-10%

In a further embodiment, these micro-spheres release the extracts upon rubbing/friction and release the fragrances upon rubbing/friction. These micro-spheres release the active ingredients upon coming in contact with the skin surface. Encapsulation prevents the loss of efficacy of the product during the time it is manufactured to the time of its use. Encapsulation holds the fragrances until the product is actually in use. Encapsulation increases the efficacy of the active ingredients as being the anti-inflammatory agents in the liner.

The cotton layer may also be impregnated with aluminum and/or magnesium hydroxide stearate and corn starch for better hygiene.

In further embodiment of the invention adapted specifically for consumers who suffer from repeat fungal infections in the form of red itchy rashes under the breasts, the central layer of the liner can further include or alternative be impregnated with Miconazole 2% powder/spray/lotion (in the form of powder, topical creams and sprays). The presence of an effective anti-fungal agent in the central layer of the liner provides a constant barrier against fungal infections throughout the day. The antifungal agent in combination with natural anti-inflammatory properties of the aforementioned plants and selenium encapsulation prevent repeat infections from bacteria and fungi as well as provide a pleasant fragrance lasting all day long.

Bra-liners may include bottom layer adhesive sides 16, for use as a liner on the inside of the brassiere. The bra-liner could be smaller sized or larger sized. The adhesive 16*a* on the bottom layer is packaged as a peel and stick application (with a sign "peel here").

The wider ends of the bra-liners are attached to one another with a dashed perforated line in the middle marked—"tear here".

The wider ends 16*b* are intended to be adhered to the center of the brassiere on the inside. The tapered ends 16*c* are intended to be adhered to the outer edge/side on the inside of the brassiere. The convex side 18*b* of the bra-liner (lower side) will be aligned along the curve of the brassiere on the lower side. The concave side 18*c* of the bra-liner is aligned facing the top of the brassiere. The transparent edges 18 of the bra-liner remain within the confines of the brassiere and are not visible from the outside. The bra-liner can be easily peeled off the brassiere by gently lifting the transparent edge and peeling off the liner in its entirety.

Figure 5:
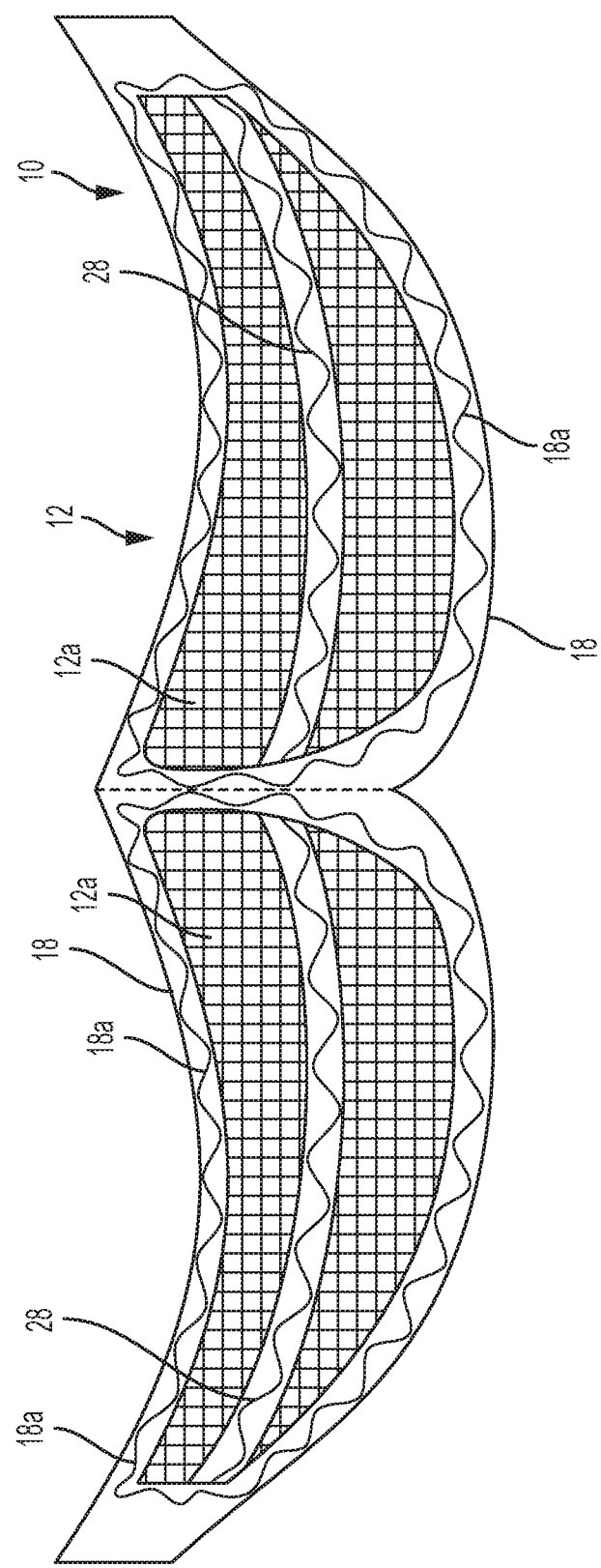
FIG. 5 is another plan view of the bottom surface of a bra-liner of FIG. 4.

Another preferred embodiment of bra-liner (FIG. 4) with self-adhesive surface 28 extending across top surface 12 and thin mesh 12*a* is designed specifically for consumers who prefer not to wear a brassiere and have problems with sweating and moisture retention. Still, consumers who wear a brassiere can also wear this liner. The liner is designed to adhere to the skin surface instead of the brassiere. The possibility of skin irritation due to repeat peeling and sticking of the bra-liner to the skin surface have been seriously taken into consideration. In this particular design the top surface of the liner will also serve as the adhesive side. The bottom layer does not have adhesive on the surface. The top surface has adhesive stripe 28 running across the entire length of the liner in both sizes. Additionally, the transparent mesh edges 18 also have an adhesive 18*a* on all of the four sides (FIG. 5). This type of a design will provide just enough adhesive surfaces (5 stripes instead of an entire surface) to keep the liner in place (under and around the breast) without causing skin irritation.

Referring to FIGS. 6 & 7, preferred embodiments of panty-liners 30 according to the invention in two of several basic sizes are illustrated. The panty-liners can be made in two or more sizes, for example, small to medium and medium to large. They are intended for consumers with mild to moderate sweating and moderate to heavy sweating. Two or more sizes of the panty-liners require an undergarment (panty/thong, men's underwear) for their intended use. Neither of the panty-liners adheres to the skin surface. Panty-liners can be used by men as well as women, it can be appreciated by those with ordinary skill in the art that the add mixture of fragrance added to the active ingredients 14*c* can vary for men and women.

The panty-liner is designed in a way that it is easy to use, has a thickness gradient across the entire length and is shaped to fit most average sized men and women. The front end 30a of the liner is wider and slightly thicker. The back end 30b of the liner is narrower and slightly thinner. There are two basic types of panty-liners, smaller sized for mild to moderate sweating; and medium sized for moderate to heavy sweating. There are two basic types for panty liners for menstrual flow (only intended for feminine use) for regular flow and for heavy menstrual flow. The maximum length of the panty-liner is preferably up to 20 cm (line a-b FIG. 6). The maximum width of the panty-liner is preferably up to 10 cm (line c-d FIG. 6). The maximum thickness of the panty-liner is preferably up to 10-mm of top surface through central layer and bottom surface.

There are two surfaces to the panty-liners and underwear-liner, namely, top surface 30c (water-permeable) and the bottom surface 30d (water-impermeable). Both surfaces are made of transparent material.

The top surface 30c comprises of a thin mesh coated with a top coat dimethicone and talcum. The mesh will allow the droplets of sweat and moisture to be diffused through it in order to be absorbed by a central layer 30e thereby leaving the top surface completely dry. The dimethicone and talcum coating will allow for a rather silky smooth surface that will prevent chaffing, rubbing against the skin, irritation from the liner and yet be hypoallergenic at the same time. As shown in FIG. 7 the top surface, central layer and bottom surface each fill entire area of panty-liner within perimeter line L. In FIG. 7, top surface and central layer are broken away to show surfaces beneath.

The bottom layer is comprised of an extra-thin plastic/polyester layer that will provide the grounds for all the layers of the liner. The backside (exterior side) of the bottom layer may have adhesive (dash lines) 30g on it.

The two layers tightly encase a central liner and taper at the edges in the form of a thin transparent edge 30f (approx. 0.5 cm wide) which will be consistent throughout the entire edge of the liner. The transparent edge may not have the adhesive on its backside.

The designs will be similar for panty-liner as well as an underwear liner. The panty-liner and underwear-liner with bottom adhesive sides have similar designs.

Panty-liners with adhesive 30g on the bottom layer are used as a liner on the inside of a panty-thong or a men's underwear. The panty-liner could be smaller sized or larger sized. The adhesive on the bottom layer can be provided as a peel and stick application (with a sign "peel here").

The wider end 30a of the panty-liner is the front end and the tapered end 30b is intended to be adhered to the back side.

The transparent edges 30f of the panty-liner remain within the confines of the panty/thong and the men's underwear, and will not be visible form the outside The central layer 30e is comprised of loosely packed cotton fibers instead of a pressed cotton sheet. The thickness of this layer preferably varies from 1-mm to 10-mm. For a typical small to medium-sized panty-liner for mild to moderate sweating the central layer will preferably be 1-2 mm thick with a thickness gradient varying from being thicker in the center and at the front to thinner at the edges and the backside of the liner.

The color of the central layer could be pure white, shades of white, shades of nude color or purely nude.

In another embodiment of the invention the central layer can be impregnated with one or more active ingredients including natural extracts of grape, cucumber, rosemary and mint encapsulated with selenium nanoparticles. These plants/extracts are chosen based on their anti-inflammatory properties, their pleasant fragrances, and on their odor-masking properties.

The selenium nanoparticles are chosen based on its antibiotic properties especially against bacteria localized to the private parts of human body.

These plants/extracts are impregnated onto the cotton fibers in the form of selenium encapsulated micro-spheres/nanoparticles. These micro-spheres release the extracts and fragrances upon rubbing/friction.

These micro-spheres release the active ingredients upon coming in contact with the skin surface.

In one embodiment for pantyliners, the composition of the active ingredients which can be provided in an aqueous solution (for anti-inflammatory properties) is preferably:

1. Grape seed oil 20%-30%
2. Rosemary 10%-20%
3. Mint 20%-30%
4. Cucumber 5%-10%
5. Menthol 5%-10%

The pantyliner can be enriched with any one or all the components of the active ingredients and enhanced with artificial fragrances.

Such encapsulation prevents the loss of efficacy of the product during the time it is manufactured to the time of its use. Encapsulation holds the fragrances until the product is actually in use, increases the efficacy of the active ingredients as being the anti-inflammatory agents in the liner.

In further embodiment of the invention adapted specifically for consumers who suffer from repeat fungal infections in the form of red itchy rashes, the central layer of the panty-liner can further include or alternative be impregnated with Miconazole 2% powder/spray/lotion. The presence of an effective anti-fungal agent in the central layer of the liner will provide a constant barrier against fungal infections throughout the day.

The antifungal agent in combination with natural anti-inflammatory properties of the aforementioned plants and selenium encapsulation will prevent repeat infections from bacteria as well as provide a pleasant fragrance lasting all day long.

The liner designed for regular and heavy menstrual flow will have a higher concentration of all the aforementioned active ingredients as the thickness of these liners will be greater than the ones indicated for sweat and moisture control allowing for greater concentration/mm3 of the liner.

Figure 10:
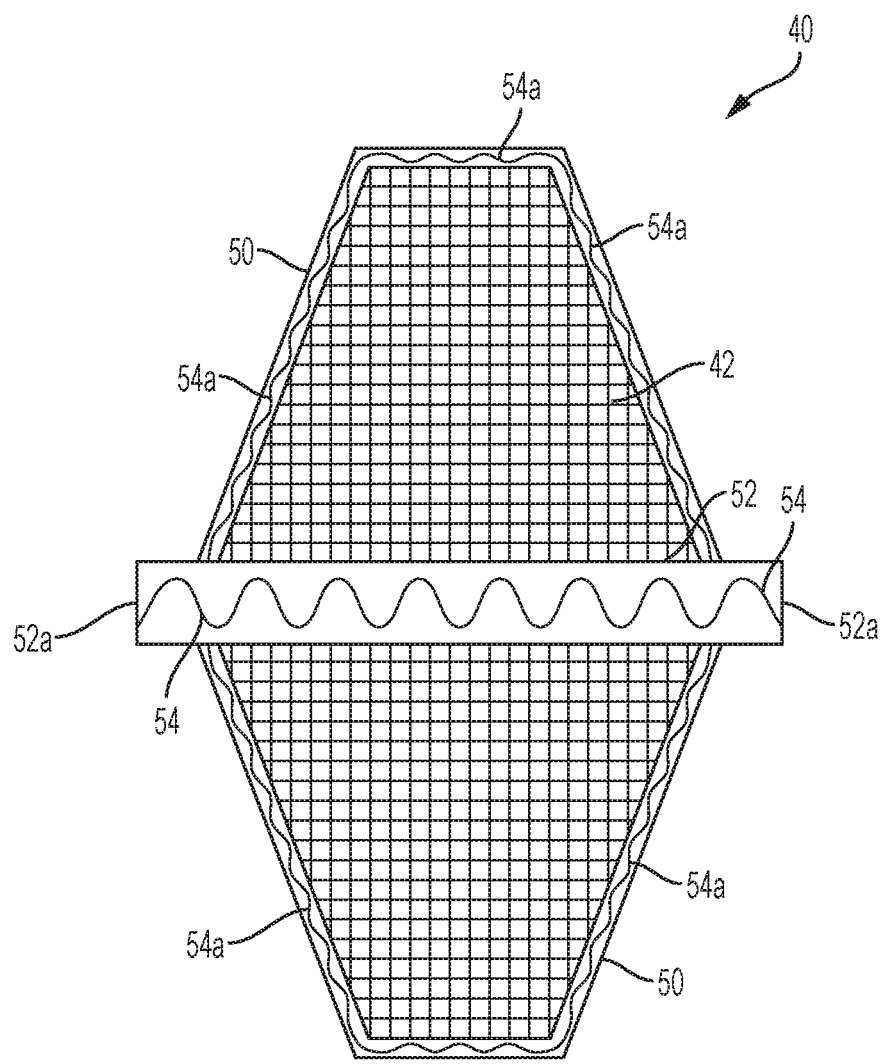
FIG. 10 is a plan view of another preferred embodiment of underarm liner showing its bottom surface.

Referring to FIGS. 8-10, preferred embodiments of two of the several basic sizes for underarm-liners based on the dimensions listed below. The underarm-liners can be made in two or more sizes (small to medium and medium to large). They are intended for consumers with mild to moderate sweating and moderate to heavy sweating in the underarm area. Both sizes of the underarm-liners require a shirtsleeve for their intended use as it will be adhered to the seam-line. Both sizes of underarm liners can be adhered directly to the underarm skin surface as well thereby eliminating the need for a shirt sleeve. Underarm-liners can be used by men as well as women, it can be appreciated by those with ordinary skill in the art that the add mixture of fragrance added to the active ingredients 14c can vary for men and women.

The maximum length of the underarm-liner is preferably up to 15 cm (line a-b, FIG. 9). The maximum width of the underarm-liner is preferably up to 12 cm (line c-d, FIG. 9). The maximum thickness of the underarm-liner is preferably up to 10-mm from top surface through central layer and bottom surface.

There are two surfaces to the underarm-liners, top surface 42 (water-permeable) and the bottom surface 44 (water-impermeable). Both surfaces are made of transparent material.

The top surface 42 is comprised of a thin mesh coated with dimethicone. The mesh will allow the droplets of sweat and moisture to be diffused thru it in order to be absorbed by a central layer leaving the surface completely dry. The dimethicone coating allows for a rather silky smooth surface that will prevent chaffing, rubbing against the skin, irritation from the liner and yet be hypoallergenic at the same time.

The bottom surface 44 is comprised of an extra-thin plastic/polyester layer that provides the grounds for all the layers of the liner. The backside of the bottom layer may, or may not, have the adhesive 46 on it.

The top and bottom surfaces tightly encase the central layer 48 and taper at the edges in the form of a thin transparent edge 50 (preferably approx. 0.5 cm wide) which is consistent throughout the entire edge of the liner. The transparent edge may, or may not have the adhesive on its backside.

As shown in FIG. 8 the top surface, central layer and bottom surface each fill entire area of underarm liner within perimeter line L. In FIG. 8, top surface and central layer are broken away to show surfaces beneath.

Underarm-liner with bottom adhesive sides is used as a liner on the inside of the shirtsleeve. The underarm-liner could be a smaller sized or a medium-larger sized. The adhesive on the bottom layer can be provided as a peel and stick application (with a sign "peel here"). The underarm-liner is folded in the middle (line c-d) allowing for a smaller sized packaging. The central wider part 40*b* is intended to be adhered to the shirtsleeve seam-line. The top tapered edge 40*a* with a slightly thinner surface will adhere to the sleeve side of the seam-line. The bottom tapered edge 40*c* with a slightly thicker surface will adhere towards the shirt-side of the seam-line. The transparent edges 50 of the underarm-liner remain within the confines of the shirt and the sleeve and will not be visible from the outside. The underarm-liner can be easily peeled off the shirt by gently lifting the transparent edge and peeling off the liner in its entirety.

An underarm-liner 40 (FIG. 10) with self-adhesive surface is designed specifically for consumers who have problems with sweating and moisture retention. Those who prefer can have the underarm-liner adhered directly against the underarm skin surface. Consumers who wear a sleeved shirt can also wear this underarm-liner. The liner is designed to adhere to the skin surface instead of the shirtsleeve. The possibility of skin irritation due to repeat peeling and sticking of the underarm-liner to the skin surface have been seriously taken into consideration. In this particular design the top surface of the liner will also serve as the adhesive side. The bottom layer will not have adhesive on the surface. The top surface has an adhesive stripe 52 running across the entire width of the liner in both sizes. Additionally, the transparent mesh edges 50 also have an adhesive 54 (54*a*) on 5 of the 6 sides with a 1-cm extension 52*a* in the center of the underarm liner on either side. This type of a design will provide just enough adhesive surfaces (6 stripes in total instead of an entire surface) to keep the liner in place (underarm area) without causing skin irritation The central layer 42 with active ingredients consists of loosely packed cotton fibers instead of a pressed cotton sheet. The thickness of this layer is preferably from 1-mm to 10-mm. For a typical small-sized underarm-liner for mild to moderate sweating the central layer may be 1-2 mm thick with a thickness gradient varying from being thicker in the center to thinner towards the edges.

The color of the central layer could be pure white, shades of white, shades of nude color or purely nude.

In another embodiment of the invention the central layer is impregnated with one or more active ingredients including natural extracts of grape, cucumber, rosemary and mint encapsulated with selenium nanoparticles. These plants/extracts are chosen based on their anti-inflammatory properties, on their pleasant fragrances, and on their odor-masking properties.

In one embodiment for under arm lines, the composition of the active ingredients which can be provided in an aqueous solution (for anti-inflammatory properties) is preferably:

1. grape seed oil 10%-20%
2. Rosemary 20%-30%
3. Mint 10%-20%
4. Cucumber 10%-20%
5. Menthol 5%-10%.

The underarm liner will be enriched with any one, or a mixture of all components of the active ingredients and enhanced with artificial fragrances.

The selenium nanoparticles are chosen based on its antibiotic properties especially against bacteria localized to the private parts of human body. These plants/extracts are impregnated onto the cotton fibers in the form of Selenium encapsulated micro-spheres/nanoparticles. These micro-spheres will release the extracts and the fragrances upon rubbing/friction. These micro-spheres will release the active ingredients upon coming in contact with the skin surface Such encapsulation prevents the loss of efficacy of the product during the time it is manufactured to the time of its use. Such encapsulation will hold the fragrances until the product is actually in use, increases the efficacy of the active ingredients as being the anti-inflammatory agents in the liner.

In a further embodiment of the invention adapted specifically for consumers who suffer from repeat fungal infections in the form of red itchy rashes, the central layer of the liner can further include or alternative be impregnated with Miconazole 2% powder/spray/lotion. The presence of an effective anti-fungal agent in the central layer of the liner s provides a constant barrier against fungal infections thru out the day. The antifungal agent in combination with natural anti-inflammatory properties of the aforementioned plants and Selenium encapsulation will prevent repeat infections from bacteria as well as provide a pleasant fragrance lasting all day long.

Various changes may be made to the structure embodying the principles of the invention. The foregoing embodiments are set forth in an illustrative and not in a limiting sense. The scope of the invention is defined by the claims appended hereto.

I claim:

1. A body liner comprising:
    a top mesh layer effective to allow sweat and moisture to be diffused through it leaving the top mesh layer dry;
    a bottom sweat and moisture impermeable layer providing a ground for all layers of the liner;
    the top mesh layer and bottom impermeable layer encasing a central layer, the central layer formed of cotton fibers for absorbing sweat and moisture passing through the top mesh layer, the central layer including at least one active ingredient encapsulated with selenium nanoparticles, the active ingredient consisting essentially of grape seed oil, cucumber, rosemary, mint and menthol;

an interior surface of the top mesh layer contacting an interior surface of the bottom impermeable layer without the central layer disposed therebetween forming an edge around the body liner; and the body liner having adhesive for securing the liner.

2. The body liner as defined in claim 1 wherein the cotton fibers of the central layer are impregnated with said at least one active ingredient.

3. The body liner as defined in claim 1 in which an exterior surface of the bottom impermeable layer has the adhesive for securing the liner to a garment.

4. The body liner as defined in claim 1 in which an exterior surface of the top mesh layer has the adhesive adapted to secure the liner to a body area.

5. The body liner as defined in claim 1 in which the top mesh layer is coated with at least one selected from the group consisting of dimethicone, talcum and silicone.

6. The body liner as defined in claim 1 in which the central layer is impregnated with an anti-fungal agent.

7. The body liner as defined in claim 1 sized to fit within a brassiere adapted to cover breasts, wherein the adhesive is configured to secure the liner.

8. The body liner as defined in claim 7 in which the central layer has a thickness gradient varying from being thicker toward a wider edge configured to face a center of a breast, and thinner toward an opposing narrower edge.

9. The body liner as defined in claim 7 in which the adhesive is placed on an exterior surface of the bottom sweat and moisture impermeable layer of the liner for adhering the liner to the brassiere.

10. The body liner as defined in claim 7 in which the adhesive is placed on an exterior surface of the top mesh layer of the liner for adhering the liner to skin.

11. The body liner as defined in claim 7 having a convex lower edge aligned with the curve of the brassiere on the lower side, and a concave upper edge aligned with the curve of the brassiere on the upper side.

12. A body liner sized to fit within an undergarment for covering genitalia, the body liner comprising:

a transparent water-permeable top layer;

a transparent water-impermeable bottom layer having an exterior surface coated with an adhesive for securing the liner to an undergarment, the body liner tapered such that a front end thereof is both thicker and wider than a back end thereof; and a central layer encased between the transparent water-permeable top layer and the transparent water-impermeable bottom layer wherein an interior surface of the transparent water-permeable top layer contacts an interior surface of the transparent water-impermeable layer forming a transparent edge around the body liner, the central liner impregnated with an effective amount of active ingredients, consisting essentially of grape seed oil, cucumber, rosemary, menthol, and mint with the active ingredients encapsulated with selenium nanoparticles.

13. The body liner of claim 12 wherein the transparent water-permeable top layer is a mesh coated with a mix of dimethicone and talcum.

14. A body liner sized to fit beneath an armpit, comprising:

a multilayer structure having a length and a width wherein the width is configured to be parallel to a shirtsleeve seam-line and the width is greater at a middle thereof than at a front edge and a back edge, a thickness of the middle is greater than a thickness at the front edge and a thickness at the back edge;

a central layer of the multilayer structure impregnated with an effective amount of active ingredients consisting essentially of grape seed oil, cucumber, rosemary, mint, and menthol with the active ingredients encapsulated with selenium nanoparticles; and an adhesive for securing the liner.

15. The body liner as defined in claim 14 in which an exterior side of a bottom surface has an adhesive for securing the liner to a shirt-sleeve seam line.

16. The body liner as defined in claim 14 in which a top surface has an adhesive for securing the liner to a body area.

17. The body liner as defined in claim 15 in which a top surface is coated with dimethicone.

\* \* \* \* \*